United States Patent [19]

Nishimura et al.

[11] Patent Number: 4,888,285

[45] Date of Patent: Dec. 19, 1989

[54] ENZYME IMMOBILIZATION ON A WATER-INSOLUBLE AMINO GROUP-CONTAINING CARRIER

[75] Inventors: Yuusaku Nishimura; Masahiko Ishida; Ryoichi Haga, all of Hitachi, Japan

[73] Assignee: Hitachi, Ltd., Tokyo, Japan

[21] Appl. No.: 129,163

[22] Filed: Dec. 7, 1987

[30] Foreign Application Priority Data

Dec. 8, 1986 [JP] Japan .................................. 61-290432

[51] Int. Cl.$^4$ ...................... C12N 11/14; C12N 11/02; C12N 11/10
[52] U.S. Cl. .................................... 435/176; 435/177; 435/178
[58] Field of Search ............... 435/174, 176, 177, 178, 435/180, 181, 182

[56] References Cited

U.S. PATENT DOCUMENTS

| | | | |
|---|---|---|---|
| 4,090,919 | 5/1978 | Chibata et al. | 435/178 |
| 4,337,313 | 6/1982 | Hershberger et al. | 435/177 |
| 4,681,843 | 7/1987 | Egerer et al. | 435/177 X |
| 4,760,024 | 7/1988 | Lantero, Jr. | 435/178 |

Primary Examiner—David M. Naff
Attorney, Agent, or Firm—Fay, Sharpe, Beall, Fagan, Minnich & McKee

[57] ABSTRACT

An immobilized enzyme having high activity and stability is obtained by immobilizing an enzyme on a water-insoluble amino group-containing carrier by use of a polyfunctional cross-linking agent such as glutaraldehyde in the presence of a phenolic carboxylic acid having one or more hydroxyl groups such as tannic acid. In addition to the phenolic carboxylic acid, a basic polysaccharide such as chitosan may also be present. The amino group-containing carrier may be aminated silica gel, aminated porous glass, aminated zeolite, or water insoluble crosslinked chitosen.

20 Claims, 2 Drawing Sheets

| IMMOBILIZATION METHOD | RELATIVE ACTIVITY (%) |
|---|---|
| $SiO_2$-NH2 + GA (0.5%) | ▨▨▨ ~85 |
| $SiO_2$-NH2 + TANNIC ACID (1.0%) | ▨▨▨ ~80 |
| $SiO_2$-NH2 + TANNIC ACID (1.0%) + GA (0.5%) | ▨▨▨ ~95 |
| $SiO_2$-NH2 + GALLIC ACID (1.0%) | ▨▨▨ ~80 |
| $SiO_2$-NH2 + GALLIC ACID (1.0%) + GA (0.5%) | ▨▨▨ ~85 |

GA : GLUTALALDEHYDE

ENZYME IMMOBILIZATION ON A WATER-INSOLUBLE AMINO GROUP-CONTAINING CARRIER

BACKGROUND OF THE INVENTION

1. Field of the Invention

This invention relates to a method for immobilizing the enzyme on a water-insoluble carrier and to an immobilized enzyme produced thereby.

More particularly, this invention relates to a method for immobilizing an enzyme on a water-insoluble amino group-containing carrier such as silica gel, porous glass or the like having amino groups introduced thereinto, by use of a polyfunctional crosslinking agent in the presence of a phenolic carboxylic acid having one or more hydroxyl groups such as tannic acid or the like or in the presence of a phenolic carboxylic acid having one or more hydroxyl groups and chitosan. In addition, the present invention is also directed to the immobilized enzymes obtained by said method.

According to this invention, an enzyme can be stably immobilized on a water-insoluble carrier while retaining its high activity, thereby producing an immobilized enzyme which permits continuous enzymatic reactions for a long period of time. Through the use of the immobilized enzyme of this invention, the purity of a product obtained by enzymatic reaction can be improved, the amount of enzyme used can be reduced, and the enzymatic reaction vessel required for the enzymatic process can be made more compacted.

2. Related Art Statement

Enzymatic reactions are widely used in industrial production processes of medicines, foods etc. Such enzymatic reactions have heretofore been carried out in solutions prepared by dissolving an enzyme in an aqueous solution of substrate. However, such methods require not only very complicated procedures, for example, the steps of supplying fresh enzyme while keeping the reaction conditions constant and of recovering the enzyme after the reaction, but also very troublesome procedures of separating and purifying the reaction product. In order to remove these defects, continuous enzymatic reactions directed to the use of an enzyme immobilized on a water-insoluble carrier have been investigated in recent years.

Along this line, the main methods for immobilizing enzymes include: known, for example, (1) the carrier covalent binding method, (2) the physical adsorption method or the ionic binding method, (3) the crosslinking method and (4) the entrapping method.

Among these immobilization methods, the carrier covalent binding method of (1) permits production of an immobilized enzyme in which the binding power between the carrier and the enzyme is relatively strong, but is disadvantageous in that the determination of optimal conditions for the covalent binding reaction is difficult, and that the production of an immobilized enzyme having high activity is also generally difficult. The physical adsorption method or ionic binding method of (2) permits immobilization of an enzyme by a simple procedure under mild conditions and hence the production of an immobilized enzyme having relatively high activity, but is disadvantageous in that since the binding power between the carrier and the enzyme is weak, the enzyme tends to be released from the carrier. The crosslinking method of (3) is disadvantageous in that since the crosslinking reaction is carried out under relatively severe conditions, only an immobilized enzyme having low activity can be obtained. The entrapping method of (4) is generally advantageous in that an immobilized enzyme can be produced easily at low cost, but is disadvantageous not only in that when a water-soluble polymer such as polyacrylamide is crosslinked and then gelatinized for entrapping an enzyme, the enzymic activity is unavoidably lowered, but also in that the enzyme is liable to be released from the gel formed.

As the method for immobilizing the enzyme according to the carrier covalent binding method of (1), there may be exemplified, for example, a method which comprises forming Schiff bases or peptide bonds between the functional groups (—$NH_2$, —COOH, etc.) on the surface of a carrier and the —$NH_2$, —COOH, etc. groups present in the enzyme molecules by use of a polyfunctional crosslinking agent or a condensing agent. A method comprising activating an amino group-containing carrier by use of a crosslinking agent such as glutaraldehyde, and then immobilizing glucoamylase thereon is described in Starch/Stärk 33 (1981) Nr. 2, S.52-55. Further, immobilization of glucoamylase on aminated silica gel by use of glutaraldehyde is described in Enzyme Microb. Technol., 1982, Vol. 4, Mar. pp. 89-92. However, the half life of the enzymic activity obtained by these methods is short, so that the period of time of stable saccharification produced by these immobilized enzymes is also short. Therefore, continuous saccharification using these immobilized enzymes cannot be carried out for a long period of time unless there is employed, for example, a method comprising placing a large number of reaction tanks in parallel and using them one after another. In this case, complicated apparatuses and procedures are required and the enzyme should be frequently renewed.

As another carrier covalent binding method, there is a method which comprises immersing a molded product of swollen chitin in an enzyme solution, then carrying out glutaraldehyde treatment, thereby producing an immobilized enzyme (Japanese Patent Application Kokai (Laid-Open) No. 111686/86). However in the case of such a method, it is also difficult to obtain a stably immobilized enzyme retaining high activity.

As described above, the immobilization processes of the prior art, in particular, the carrier covalent binding method, have many disadvantageous, for example, insufficient consideration has been given to the affinity of the carrier surface for the enzyme, determination of conditions for covalent binding reaction is complicated, and it is difficult to obtain an immobilized enzyme having high activity.

On the other hand, methods for producing an immobilized enzyme by the crosslinking method include, for example, a method comprising the steps of coagulating a cell enzyme by use of a macromolecule coagulant such as chitosan, and then carrying out a crosslinking reaction through the use of glutaraldehyde or the like to immobilize the cell enzyme (Japanese Patent Application Kokai (Laid-Open) No. 120182/77); a method comprising using tannin together with a coagulant such as polyethyleneimine, and then immobilizing an enzyme by use of a crosslinking agent such as glutaraldehyde (Japanese Patent Application Kokai (Laid-Open) No. 110190/82); and a method comprising the steps of using polyethyleneimine as a coagulant, carrying out a crosslinking reaction in the presence of chitosan through the use of glutaraldehyde, thereby immobilizing an enzyme (Japanese Patent Application Kokai (Laid-Open) No. 58072/85). These methods use chitosan or tannin, but in all of them, immobilized enzymes are obtained by the crosslinking methods. Thus, they are different from the carrier covalent binding method in which an enzyme is immobilized on a water-soluble carrier.

SUMMARY OF THE INVENTION

An object of this invention is to provide an immobilized enzyme having high activity and stability by simple covalent binding reaction of the surface of a water-insoluble carrier with an enzyme.

Another object of this invention is to provide a method for the immobilization of an enzyme wherein the enzyme is stably immobilized on a water-insoluble amino group-containing carrier while retaining its high activity.

Other and further objects and advantages of this invention will be apparent from the following description.

The above objects and advantages of this invention can be achieved by carrying out the covalent binding reaction of an enzyme with the surface of a carrier containing amino groups as surface functional groups in the presence of a substance having specific adsorbability for enzymes, i.e., a phenolic carboxylic acid having one or more hydroxyl groups, preferably in the presence of a phenolic carboxylic acid having one or more hydroxyl groups and a basic polysaccharide having high adsorbability for enzymes such as chitosan, and thereby obtaining an immobilized enzyme.

That is to say, a first feature of the invention is a method for the immobilization of an enzyme which comprises immobilizing an enzyme in an aqueous solution containing the enzyme on a water-insoluble carrier having amino groups in the molecule, said immobilization being carried out by covalent binding reaction of the enzyme with the water-insoluble carrier through a polyfunctional crosslinking agent in the presence of a phenolic carboxylic acid having one or more hydroxyl groups.

A second feature of the invention is a method for the immobilization of an enzyme which comprises immobilizing an enzyme in an aqueous solution containing the enzyme on a water-insoluble carrier containing amino groups in the molecule, said immobilization being carried out by covalent binding reaction of the enzyme with the carrier through a polyfunctional crosslinking agent in the presence of a phenolic carboxylic acid having one or more hydroxyl groups and a basic polysaccharide having high adsorbability for enzymes.

A third feature of the invention is a method for the immobilization of an enzyme which comprises forming Schiff bases between a water-insoluble carrier having amino groups in the molecule and an enzyme in an aqueous solution containing the enzyme by use of a polyfunctional crosslinking agent, and thereby immobilizing the enzyme, said Schiff base formation being carried out in the presence of a phenolic carboxylic acid having one or more hydroxyl groups.

A fourth feature of the invention is a method for the immobilization of an enzyme which comprises forming Schiff bases between a water-insoluble carrier having amino groups in the molecule and an enzyme in an aqueous solution containing the enzyme by use of a polyfunctional crosslinking agent, and thereby immobilizing the enzyme, said Schiff base formation being carried out in the presence of a phenolic carboxylic acid having one or more hydroxyl groups and a basic polysaccharide having high adsorbability for enzymes.

A fifth feature of the invention is an immobilized enzyme obtained by the immobilization on a water-insoluble carrier by use of a polyfunctional crosslinking agent, said immobilization being carried out by adsorption of an enzyme on a phenolic carboxylic acid having one or more hydroxyl groups, followed by covalent binding reaction of the amino groups of the water-insoluble carrier and the amino groups of the enzyme with the functional groups of the crosslinking agent.

A sixth feature of the invention is an immobilized enzyme obtained by the immobilization on a water-insoluble carrier by use of a polyfunctional crosslinking agent, said immobilization being carried out by adsorption of an enzyme on a phenolic carboxylic acid having one or more hydroxyl groups and a basic polysaccharide having high adsorbability for enzymes, followed by covalent binding reaction of the amino groups of the water-insoluble carrier and the amino groups of the enzyme with the functional groups of the crosslinking agent.

A seventh feature of the invention is an immobilized enzyme obtained by the immobilization on a water-insoluble carrier by use of a polyfunctional crosslinking agent, said immobilization being carried out by adsorption of an enzyme on a phenolic carboxylic acid having one or more hydroxyl groups, followed by formation of Schiff bases between the functional groups of the crosslinking agent and the amino groups of the water-insoluble carrier and of the enzyme.

An eighth feature of the invention is an immobilized enzyme obtained by the immobilization on a water-insoluble carrier by use of a polyfunctional crosslinking agent, said immobilization being carried out by adsorption of an enzyme on a phenolic carboxylic acid having one or more hydroxyl groups and a basic polysaccharide having high adsorbability for enzymes, followed by formation of Schiff bases between the functional groups of the crosslinking agent and the amino groups of the water-insoluble carrier and of the enzyme.

DETAILED DESCRIPTION OF THE INVENTION

Figures 1, 2:
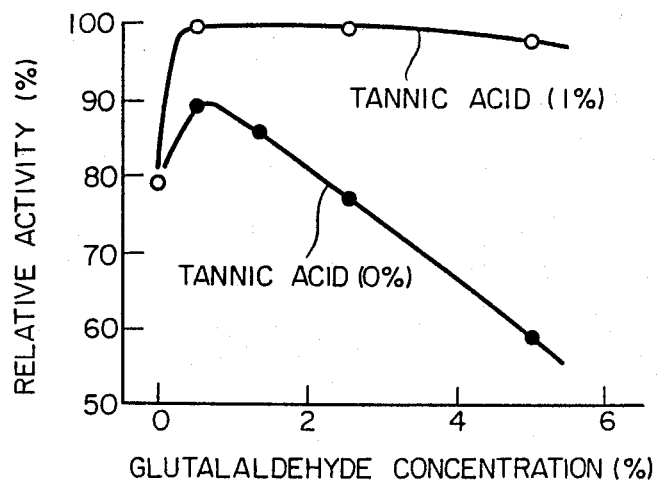
FIG. 1 is a graph showing the relationship between glutaraldehyde concentration and the activity of a carrier having glucoamylase immobilized thereon.
FIG. 2 is a bar graph showing comparison of the activities of carriers having glucoamylase immobilized thereon which were obtained by immobilization on aminated silica gel by various methods.

The water-insoluble amino group-containing carrier used in this invention includes, for example, water-insoluble aminated carriers obtained by introducing amino groups into silica gels, porous glasses, zeolites, etc. through silane coupling reaction using an aminosilane derivative, and amino polysaccharide carriers obtained by crosslinking chitosan formed by deacetylation of chitin and thereby insolubilizing the same.

As a method for covalent binding of an enzyme to amino groups which are functional groups on the surface of said water-insoluble carrier, a method comprising forming Schiff bases between these amino groups and the amino groups in the enzyme is preferred. When glutaraldehyde is used as a polyfunctional crosslinking agent, the formation of the Schiff bases is represented by the formula (1) shown below. The polyfunctional agent includes polyaldehydes such as glutaraldehyde, dialdehyde starch, malonaldehyde, succinic aldehyde, etc. Among them, glutaraldehyde is particularly preferred.

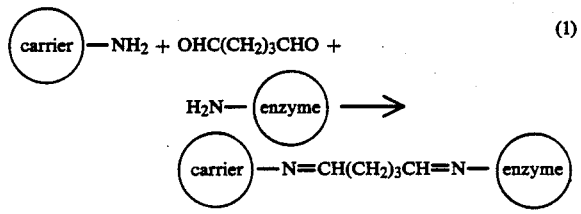

(1)

In this invention, an enzyme is immobilized in the presence of a substance having specific adsorbability for enzymes. Such a substance includes, for example, phenolic carboxylic acids having one or more hydroxyl groups such as tannic acid, pyrogallol tannin, gallic acid, catechol and the like. Among the phenolic carboxylic acids, tannic acid is particularly preferred. In this invention, it is preferable to use basic polysaccharides having high adsorbability for enzymes, together with the phenolic carboxylic acids. As such polysaccharides, chitosan which is a chitin derivative is exemplified.

As the enzyme used in this invention, any enzyme may be used so long as it is adsorbed on tannic acid, chitosan or the like without losing its activity. Said enzyme includes, for example, glucoamylase, $\beta$-amylase, $\alpha$-amylase, glutamate decarboxylase, glucose isomerase and inulase.

A desired immobilized enzyme is preferably obtained by placing an enzyme-containing aqueous solution together with a water-insoluble amino group-containing carrier, a polyfunctional crosslinking agent, and a phenolic carboxylic acid having one or more hydroxyl groups alone or a combination of a phenolic carboxylic acid having one or more hydroxyl groups and chitosan, and carrying out the reaction at 5° to 40° C. for several hours.

The shape of the water-insoluble amino-group-containing carrier is preferably granular or bead-like, and its size is preferably about 0.1 to about 5 mm, particularly preferably about 0.2 to about 0.5 mm. When the size is too large, the void volume is increased, so that the enzymic activity per volume is decreased. On the other hand, when the size is too small, the pressure loss becomes too large or separation of the immobilized enzyme from the reaction mixture becomes difficult. Therefore, it is not desirable.

The pH of the reaction mixture at the time of enzyme immobilization is in the range where the enzyme is not deactivated. The reaction temperature is in the range where no thermal deactivation occurs, and is, in practice, preferably in the range of 5° to 40° C. The reaction time is 1 to 10 hours. When the reaction temperature is high, the reaction time may be short and shaking or stirring is recommendable for carrying out the reaction efficiently. At the time of immobilization, the amount of the solution containing an enzyme and the like is 5 to 10 times that of the carrier. When the amount of the solution is too small, the carrier tends to be broken by shaking or stirring at the time of the reaction. On the other hand, the amount of the solution is too large, the rate of immobilization reaction is decreased.

In the invention, the amount of the polyfunctional crosslinking agent used for the enzyme immobilization is preferably stoichiometrical with regard to the amino groups of the carrier. In the invention, as described hereinafter, the polyfunctional crosslinking agent need not be used in excess, but even when it is used in excess, an immobilized enzyme having sufficiently high activity can be obtained.

The amount of the phenolic carboxylic acid used for the enzyme immobilization is usually about 0.1% by weight or more, preferably about 0.1% to about 10% by weight based on the weight of the enzyme-containing aqueous solution.

The amount of the basic polysaccharide having high adsorbability for enzymes such as chitosan or the like is usually preferably about 0.01% to about 0.1% by weight based on the weight of the enzyme-containing aqueous solution.

In order to obtain an immobilized enzyme having high activity, it is preferable to remove enzyme which is liable to be released because of insufficient binding, the surplus polyfunctional crosslinking agent, and the enzyme adsorbents such as tannic acid, chitosan, etc. by washing a carrier having enzyme immobilized thereon, sufficiently with a suitable buffer solution after reaction of the polyfunctional crosslinking agent.

In a method comprising forming Schiff bases between the amino groups on the surface of a water-insoluble amino group-containing carrier and the amino groups in enzyme molecules by use of a polyfunctional crosslinking agent such as glutaraldehyde or the like, and thereby immobilizing the enzyme, glutaraldehyde or the like as polyfunctional crosslinking agent should be present generally in a stoichiometric or larger amount for rapid and complete progress of the Schiff base formation reaction. However, it is difficult to obtain an immobilized enzyme having high activity by such an immobilization method because when a large amount of a polyfunctional crosslinking agent is present, a part of enzyme molecules to be immobilized are chemically modified, so that the higher-order structure of the active site of the protein is broken resulting in deactivation of the enzyme. Therefore, in conventional immobilization methods, there is unavoidably employed a method which comprises previously treating an amino group-containing carrier with an excess of polyfunctional crosslinking agent to activate the carrier, removing the unreacted polyfunctional crosslinking agent, and then reacting an enzyme with the carrier to immobilize the same thereon. But this method is disadvantageous in that since crosslinking reaction of the amino groups of the carrier with one another proceeds considerably and hence functional groups which react with an enzyme to be immobilized are decreased in number, the amount of enzyme immobilized is decreased, so that the activity of the resulting carrier having enzyme immobilized thereon is generally low.

On the other hand, it has been found that when as in this invention, covalent binding reaction of the amino groups of a carrier with an enzyme by use of a polyfunctional crosslinking agent is carried out in the presence of a substance having specific adsorbability for enzymes, for example, a phenolic carboxylic acid having one or more hydroxyl groups such as tannic acid or the like or chitosan together therewith, deactivation of the enzyme can be prevented, so that an immobilized enzyme having high activity and stability can be obtained, even when the polyfunctional crosslinking agent is present in excess.

The reason why the immobilized enzyme of this invention obtained by using a phenolic carboxylic acid having one or more hydroxyl groups has high activity seems to be as follows. The phenolic carboxylic acid which has specific adsorbability for enzymes adsorbs a larger amount of enzyme to stabilize the higher-order structure of this enzyme, so that deactivation by the polyfunctional crosslinking agent is prevented. Moreover, the amino groups of the carrier and the amino groups of the enzyme are linked to each other through the polyfunctionals groups of the polyfunctional crosslinking agent, so that the enzyme is strongly immobilized on the carrier.

The reason why the immobilized enzyme of this invention obtained by using a basic polysaccharide together with a phenolic carboxylic acid having one or more hydroxyl groups, preferably chitosan, has still higher activity seems to be as follows. Chitosan is a basic polysaccharide and has high adsorbability for enzymes, and therefore when chitosan is present together with a phenolic carboxylic acid having one or more hydroxyl groups, enzyme is adsorbed on the both in common, so that its higher-order structure becomes still stronger.

As described above in detail, according to this invention, enzyme can be immobilized on a water-insoluble carrier stably while retaining its high activity, and there can be obtained an immobilized enzyme which permits continuous enzymatic reaction for a long period of time. Therefore, by use of the immobilized enzyme of this invention, the purity of a product obtained by enzymatic reaction can be improved, the amount of enzyme to be used can be reduced, and an enzymatic reaction vessel can be made more compacted.

This invention is concretely illustrated below with reference to an Example for the a method for immobilization of glucoamylase derived from *Aspergillus niger* which is used mainly for the saccharification of starch. In addition, this invention is concretely illustrated with reference to Examples for methods for the immobilization of α-amylase and glutamate decarboxylase, respectively.

EXAMPLE 1

Immobilization of glucoamylase

Silica gel (particle diameter 0.3 φ, pore diameter 500Å) was aminated with γ-aminotriethoxysilane in toluene to prepare a carrier (hereinafter referred to $SiO_2$—$NH_2$ in some cases), and 1 ml of the carrier was kept in contact with 10 ml of an aqueous solution (0.05 M acetate buffer, pH 4.5) containing 0.5 ml of glucoamylase (3000 U/ml), at room temperature for 4 hours to carry out immobilization. Then, the thus treated carrier was washed with 0.05 M acetate buffer (pH 4.5) to remove the surplus glucoamylase, whereby immobilized glucoamylase was obtained. Stable immobilization was variously attempted by properly adding glutaraldehyde, tannic acid (in an amount of 1.0% by weight based on the weight of the glucoamylase-containing aqueous solution), chitosan (in an amount of 0.05% by weight based on the weight of the glucoamylase-containing aqueous solution), etc. alone or in combination of two or more thereof at the time of the immobilization reaction.

Determination of the Activity of Carriers Having Glucoamylase Immobilized Thereon 15 ml of a 30% aqueous dextrin solution (pH 4.5) was kept in contact, under shaking at 60° C., with 1 ml of each of carriers having glucoamylase immobilized thereon which had been obtained by carrying out immobilization reaction in the presence or absence of tannic acid by use of various concentrations of glutaraldehyde or with 1 ml of each of carriers having glucoamylase immobilized thereon which had been obtained in the presence of tannic acid or gallic acid by or without using glutaraldehyde. Then, the concentration of glucose produced was measured, whereby the relative activity of each carrier having glucoamylase immobilized thereon was determined. The proportion of reducing sugar of the dextrin used as substrate was 18%.

The results obtained are shown in FIG. 1 and FIG. 2.

FIG. 1 shows the relationship between glutaraldehyde concentration and the activity of an immobilized product in the case where glucoamylade was immobilized on aminated silica gel by using a polyfunctional crosslinking agent glutaraldehyde. When tannic acid which is one of the phenolic carboxylic acids is present in the immobilization reaction, an immobilized product having high activity can be obtained in a wide glutaraldehyde concentration range. On the other hand, when tannic acid is absent, the activity of immobilized product is seriously affected by the glutaraldehyde concentration, and the optimum glutaraldehyde concentration range is very narrow. In addition, the activity of immobilized product is sharply lowered with an increase of the glutaraldehyde concentration. As it generally known, most enzymes are denatured by organic solvents to be deactivated. The reason why the activity of the immobilized product obtained in the absence of tannic acid is low is that glucoamylase is deactivated by glutaraldehyde. From the above, it can be seen that in this invention, the optimum glutaraldehyde concentration is stoichiometrical with regard to the amino groups of a carrier, as shown by the formula (1) mentioned hereinbefore. For preventing the deactivation of glucoamylase by glutaraldehyde, it was sufficient that tannic acid was present in a very small amount of, preferably about 0.1 per cent by weight, more preferable several per cent by weight based on the weight of the glucoamylase-containing aqueous solution. It was found that when the covalent binding reaction of an aminated carrier with glucoamylase by use of glutalaldehyde was carried out in the presence of tannic acid, the enzyme was not deactivated and even when a sufficient amount of glutaraldehyde was used, the reaction proceeded rapidly and completely, so that there could be obtained a carrier having glucoamylase immobilyzed thereon which had high activity and stability.

FIG. 2 shows comparison of the activities of carriers having glucoamylase immobilized thereon which were obtained by immobilizing glucoamylase on aminated silica gel ($SiO_2$—$NH_2$) by various immobilization methods. It can be seen that in the case of a method using a phenolic carboxylic acid having one or more hydroxyl groups such as tannic acid, gallic acid, etc., the activity is higher than in the case of a conventional method using glutaraldehyde (GA) alone.

Theremostability Test on Carriers Having Glucoamylase Immobilized Thereon 1 ml of each carrier having glucoamylase immobilized thereon which had been obtained using tannic acid or catechol was kept in contact with 15 ml of a 30% aqueous glucose solution (pH 4.5) at 60° C., and after heat treatment, the residual activity of this immobilized product was measured.

Figure 3:
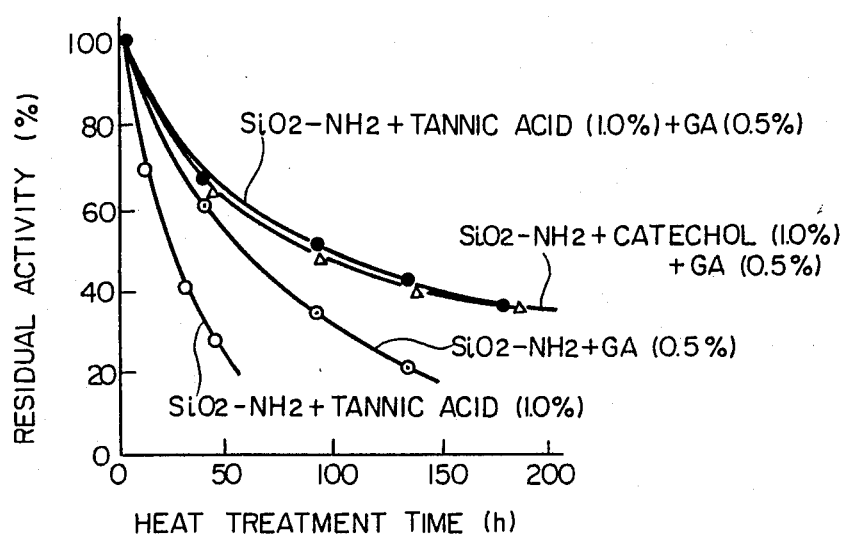
FIG. 3 is a graph showing the thermostability of carriers having glucoamylase immobilized thereon which were obtained by various methods.

The results obtained were as shown in FIG. 3.

FIG. 3 shows the thermostability of carriers having glucoamylase immobilized thereon. The activity of the immobilized products obtained by use of a phenolic carboxylic acid having one or more hydroxyl groups such as tannic acid or catechol is high. But employment of a phenolic carboxylic acid having one or more hydroxyl groups alone is not desirable because glucoamylase adsorbed thereon is merely deposited on the surface of a carrier, so that glucoamylase is easily released by longtime heat-treatment, resulting in a rapid lowering of the residual activity.

On the other hand, in the case of a conventional immobilized product obtained by use of glutaraldehyde alone, glucoamylase is immobilized by covalent binding to the amino groups of a carrier, so that glucoamylase is not easily released, and its deactivation mainly accompanies thermal denaturation and the lowering of the residual activity by heat treatment is appreciably lessened. On the other hand, in the case of the immobilized product of this invention obtained by use of a phenolic carboxylic acid having one or more hydroxyl groups and glutaraldehyde, the lowering of the residual activity is still slighter, indicating that this immobilized product is excellent in thermostability.

Continuous Saccharification of Dextrin

A column (inside diameter: 16 φ) maintained at 55° C. was packed with 20 ml of each carrier having glucoamylase immobilized thereon which had been obtained using tannic acid alone or a combination of tannic acid and chitosan, and a 30% aqueous dextrin solution (pH 4.5) was passed therethrough at a flow rate of 1 ml/min, whereby continuous saccharification of dextrin was carried out.

Figure 4:
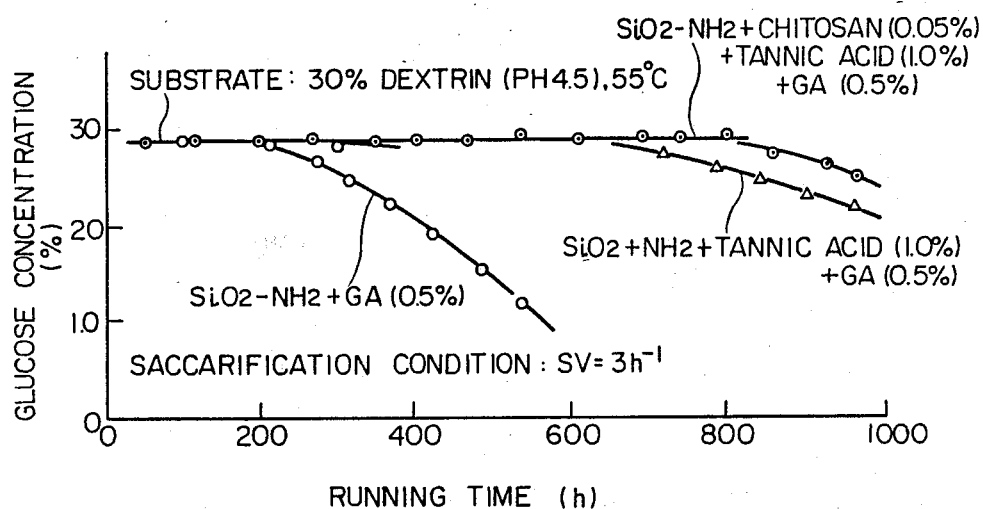
FIG. 4 is a graph showing the test results of continuous saccharification of dextrin by carriers having glucoamylase immobilized thereon which were obtained by various methods.

The results obtained are shown in FIG. 4.

FIG. 4 shows test results of continuous saccharification of dextrin by each carrier having glucoamylase immobilized thereon. The stable saccharification time in the case of immobilized glycoamylase obtained by immobilization using glutaraldehyde together with tannic acid which is one of the phenolic carboxylic acids is about twice that in the case of immobilized glucoamylase obtained by glutaraldehyde alone according to a conventional method. Furthermore, the stable saccharification time in the case of immobilized glucoamylase obtained by using chitosan, a chitin derivative in combination with glutaraldehyde and tannic acid is about 3 times that in the case of the latter immobilized glucoamylase.

In addition, when tannic acid alone is used together with glutaraldehyde, the environment of enzyme is an acidic atmosphere, while when a combination of chitosan and tannic acid is used together with glutaraldehyde, the environment of enzyme becomes a neutral atmosphere and this condition seems to have a beneficial effect on the thermostability of immobilized glucoamylase. Although the adding amount of chitosan depends on the immobilization conditions, a sufficient effect can be obtained when the adding amount is about 0.1% by weight based on the weight of the glucoamylase-containing aqueous solution.

EXAMPLE 2

To 1 ml of aminated silica gel was added 10 ml of an aqueous solution (pH 7.0) containing 0.5 ml of α-amylase, followed by adding thereto tannic acid in an amount of 1% by weight based on the weight of the α-amylase-containing aqueous solution and glutaraldehyde in an amount of 0.5% by weight based on the weight of the α-amylase-containing aqueous solution. The aminated silica gel was thus kept in contact with the α-amylase-containing aqueous solution at room temperature for 4 hours to immobilize α-amylase.

The activity of the immobilized α-amylase was determined in the following manner, and the initial activity and the half life of activity were evaluated.

With 15 ml of a 30% aqueous potato starch solution (pH 7, Ca$^{++}$ 3 mM) was kept in contact 1 ml of the immobilized α-amylase at 80° C. for 20 minutes, and the reducing sugars produced were determined.

The half life of activity was defined as time required for the initial activity to be reduced by 50% in the case where treatment in an aqueous solution (pH 7.0) at 80° C. was carried out.

COMPARATIVE EXAMPLE 2

To 1 ml of aminated silica gel was added 10 ml of an aqueous solution (pH 7.0) containing 0.5 ml of α-amylase, followed by adding thereto glutaraldehyde (0.5% by weight). The aminated silica gel was thus kept in contact with the aqueous solution at room temperature for 4 hours to immobilized α-amylase.

EXAMPLE 3

To 1 ml of aminated silica gel was added an aqueous solution (pH 5.0) containing 20 mg of glutamate decarboxylase, followed by adding thereto tannic acid (1% by weight) and glutaraldehyde (0.5% by weight). The aminated silica gel was thus kept in contact with the aqueous solution at room temperature for 2 hours to immobilize glutamate decarboxylase.

The activity of the immobilized enzyme was determined in the following manner, and the initial activity and the half life of activity were evaluated.

With 15 ml of a 0.05 M aqueous glutamic acid solution (pH 5.0) was kept in contact 1 ml of the immobilized enzyme at 37° C. for 30 minutes, and the γ-aminobutyric acid produced was determined.

The half life of activity was defined as time required for the initial activity to be reduced by 50% in the case where treatment in an aqueous solution (pH 5.0) at 45° C. was carried out.

COMPARATIVE EXAMPLE 3

To 1 ml of aminated silica gel was added an aqueous solution (pH 5.0) containing 20 mg of glutamate decarboxylase, followed by adding thereto glutaraldehyde (0.5% by weight). The aminated silica gel was thus kept in contact with aqueous solution at room temperature for 2 hours to immobilize glutamate decarboxylase.

EXAMPLE 4

To 1 ml of aminated silica gel was added 10 ml of an aqueous solution (pH 7.5) containing 50 mg of glucose isomerase, followed by adding thereto tannic acid (1% by weight) and glutaraldehyde (0.5% by weight). The aminated silica gel was thus kept in contact with the aqueous solution at room temperature for 4 hours to immobilize glucose isomerase.

The activity of the immobilized glucose isomerase was determined in the following manner, and the initial activity and the half life of activity were evaluated.

With 15 ml of a 30% aqueous glucose solution (pH 7.5, $Mg^{++}$ 0.01 M) was kept in contact 1 ml of the immobilized glucose isomerase at 65° C. for 1 hour, and the fructose produced was determined.

The half life of activity was defined as time required for the initial activity to be reduced by 50% in the case where treatment in an aqueous solution (pH 7.5) at 70° C. was carried out.

COMPARATIVE EXAMPLE 4

To 1 ml of aminated silica gel was added 10 ml of an aqueous solution (pH 7.5) containing 50 mg of glucose isomerase, followed by adding thereto glutaraldehyde (0.5% by weight). The aminated silica gel was thus kept in contact with the aqueous solution at room temperature for 4 hours to immobilize glucose isomerase.

EXAMPLE 5

To 1 ml of aminated silica gel was added 10 ml of an aqueous solution (pH 6.0) containing 100 mg of inulase, followed by adding thereto tannic acid (1% by weight) and glutaraldehyde (0.5% by weight). The aminated silica gel was thus kept in contact with the aqueous solution at room temperature for 4 hours to immobilize inulase.

The activity of the immobilized inulase was determined in the following manner, and the initial activity and the half life of activity were evaluated.

With 15 ml of a 10% aqueous inulin solution (pH 6.0) was kept in contact 1 ml of the immobilized inulase at 40° C. for 30 minutes, and the fructose produced was determined.

The half life of activity was defined as time required for the initial activity to be reduced by 50% in the case where treatment in an aqueous solution (pH 6.0) at 45° C. was carried out.

COMPARATIVE EXAMPLE 5

To 1 ml of aminated silica gel was added 10 ml of an aqueous solution (pH 6.0) containing 100 mg of inulase, followed by adding thereto glutaraldehyde (0.5% by weight). The aminated silica gel was thus kept in contact with the aqueous solution at room temperature for 4 hours to immobilize inulase.

The initial activities and the half lives of activity in Examples 2, 3, 4 and 5 and Comparative Examples 2, 3, 4 and 5 are shown in Table 1. It can be seen from Table 1 that when an enzyme is immobilized on an amino group-containing carrier by covalent binding by using a polyfunctional crosslinking agent glutaraldehyde, the presence of tannic acid is effective in improving the initial activity and thermostability of the immobilized enzyme.

TABLE 1

|  | Initial activity (relative value) | Half life of activity (relative value) |
|---|---|---|
| Example 2 | 100 | 100 |
| Comparative Example 2 | 81 | 91 |
| Example 3 | 100 | 100 |
| Comparative Example 3 | 94 | 97 |

TABLE 1-continued

|  | Initial activity (relative value) | Half life of activity (relative value) |
|---|---|---|
| Example 4 | 100 | 100 |
| Comparative Example 4 | 93 | 69 |
| Example 5 | 100 | 100 |
| Comparative Example 5 | 76 | 73 |

What we claim is:

1. A method for immobilizing an enzyme on a water-insoluble carrier comprising the steps of:
   (a) adding a phenolic carboxylic acid having one or more hydroxyl groups to an aqueous solution containing an enzyme;
   (b) permitting said enzyme to be absorbed on said phenolic carboxylic acid;
   (c) adding to the solution a water-insoluble amino group-containing carrier and a polyfunctional crosslinking agent;
   (d) permitting said enzyme absorbed on said phenolic carboxylic acid to bind with said water-insoluble amino group-containing carrier through said polyfunctional crosslinking agent; and,
   (e) recovering the resultant immobilized enzyme on a water-insoluble carrier from the aqueous solution.

2. The method for immobilization of enzyme according to claim 1, wherein the water-insoluble carrier containing amino groups is aminated silica gel, aminated porous glass, aminated zeolite, or water-insoluble cross-linked chitosan.

3. The method for immobilization of enzyme according to claim 1, wherein the polyfunctional crosslinking agent is a polyaldehyde.

4. The method for immobilization of enzyme according to claim 3, wherein the polyaldehyde is glutaraldehyde.

5. The method for immobilization of enzyme according to claim 1, wherein the phenolic carboxylic acid is tannic acid, gallic acid or catechol.

6. The method for immobilization of enzyme according to claim 1, wherein the phenolic carboxylic acid is tannic acid.

7. A method for immobilizing an enzyme on a water-insoluble carrier comprising the steps of:
   (a) adding a phenolic carboxylic acid having one or more hydroxyl groups and a basic polysaccharide having high adsorbability for enzymes to an aqueous solution containing an enzyme;
   (b) permitting said enzyme to be absorbed on said phenolic carboxylic acid and said basic polysaccharide;
   (c) adding to the solution a water-insoluble amino group-containing carrier and a polyfunctional crosslinking agent;
   (d) permitting said enzyme absorbed on said phenolic carboxylic acid and said basic polysaccharide to bind with said water-insoluble amino group-containing carrier through said polyfunctional crosslinking agent; and,
   (e) recovering the resultant immobilized enzyme on a water-insoluble carrier from the aqueous solution.

8. The method for immobilization of enzyme according to claim 7, wherein the basic polysaccharide having high adsorbability for enzymes is chitosan.

9. The method for immobilization of enzyme according to claim 7, wherein the water-insoluble carrier containing amino groups is aminated silica gel, aminated porous glass, aminated zeolite, or water-insoluble crosslinked chitosan.

10. The method for immobilization of enzyme according to claim 7, wherein the polyfunctional crosslinking agent is glutaraldehyde.

11. The method for immobilization of enzyme according to claim 7, wherein the phenolic carboxylic acid is tannic acid.

12. An immobilized enzyme produced by a method for immobilizing an enzyme on a water-insoluble carrier comprising the steps of:
    (a) adding a phenolic carboxylic acid having one or more hydroxyl groups to an aqueous solution containing an enzyme;
    (b) permitting said enzyme to be absorbed on said phenolic carboxylic acid;
    (c) adding to the solution a water-insoluble amino group-containing carrier and a polyfunctional crosslinking agent;
    (d) permitting said enzyme absorbed on said phenolic carboxylic acid to bind with said water-insoluble amino group-containing carrier through said polyfunctional crosslinking agent; and,
    (e) recovering the resultant immobilized enzyme on a water-insoluble carrier from the aqueous solution.

13. The immobilized enzyme according to claim 12, wherein the water-insoluble carrier is aminated silica gel, aminated porous glass, aminated zeolite, or water-insoluble crosslinked chitosan.

14. The immobilized enzyme according to claim 12, wherein the polyfunctional crosslinking agent is glutaraldehyde.

15. The immobilized enzyme according to claim 12, wherein the phenolic carboxylic acid is tannic acid.

16. An immobilized enzyme produced by a method for immobilizing an enzyme on a water-insoluble carrier comprising the steps of:
    (a) adding a phenolic carboxylic acid having one or more hydroxyl groups and a basic polysaccharide having high adsorbability for enzymes to an aqueous solution containing an enzyme;
    (b) permitting said enzyme to be absorbed on said phenolic carboxylic acid and said basic polysaccharide;
    (c) adding to the solution a water-insoluble amino group-containing carrier and a polyfunctional crosslinking agent;
    (d) permitting said enzyme absorbed on said phenolic carboxylic acid and said basic polysaccharide to bind with said water-insoluble amino group-containing carrier through said polyfunctional crosslinking agent; and,
    (e) recovering the resultant immobilized enzyme on a water-insoluble carrier from the aqueous solution.

17. The immobilized enzyme according to claim 16, wherein the basic polysaccharide having high adsorbability for enzymes is chitosan.

18. The immobilized enzyme according to claim 16, wherein the water-insoluble carrier is aminated silica gel, aminated porous glass, aminated zeolite, or water-insoluble crosslinked chitosan.

19. The immobilized enzyme according to claim 16, wherein the polyfunctional crosslinking agent is glutaraldehyde.

20. The immobilized enzyme according to claim 16, wherein the phenolic carboxylic acid is tannic acid.

* * * * *